(12) United States Patent
Feuer et al.

(10) Patent No.: US 6,287,584 B1
(45) Date of Patent: *Sep. 11, 2001

(54) FLEXIBLE HYDROPHILIC ARTICLES ESPECIALLY SPONGES, HAVING A RESIDUAL ANTIMICROBIAL EFFECT

(75) Inventors: William Ronald Feuer, Nyack, NY (US); Beverly Ann Kiefer, Montvale; Karen Ann McCue, Tenafly, both of NJ (US)

(73) Assignee: Reckitt & Colman Inc., Wayne, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/034,062

(22) Filed: Mar. 3, 1998

(30) Foreign Application Priority Data

Apr. 2, 1997 (GB) .................................................. 9706713

(51) Int. Cl.⁷ ........................................................ A01N 25/34
(52) U.S. Cl. ........................... 424/404; 424/405; 424/411; 424/413; 424/420
(58) Field of Search .................................. 424/404, 405, 424/411, 413, 420

(56) References Cited

U.S. PATENT DOCUMENTS

| | | | |
|---|---|---|---|
| 3,227,614 | 1/1966 | Scheuer | 167/84 |
| 3,283,357 | 11/1966 | Decker et al. | 15/506 |
| 3,586,520 * | 6/1971 | Dillion | 106/15 |
| 4,339,550 | 7/1982 | Palinczar et al. | 521/99 |
| 4,631,297 | 12/1986 | Battice et al. | 521/78 |
| 4,666,621 | 5/1987 | Clark et al. | 252/91 |
| 4,692,374 | 9/1987 | Bouchette | 428/288 |
| 4,704,757 | 11/1987 | Young | 15/104.94 |
| 4,737,405 | 4/1988 | Bouchette | 428/288 |
| 4,740,398 | 4/1988 | Bouchette | 428/28 |
| 4,847,089 | 7/1989 | Kramer et al. | 424/405 |
| 4,877,816 | 10/1989 | Murabayashi et al. | 521/92 |
| 4,923,607 | 5/1990 | Ninomiya et al. | 210/490 |
| 5,000,987 | 3/1991 | Ninomiya et al. | 427/246 |
| 5,091,102 | 2/1992 | Sheridan | 252/91 |
| 5,152,996 | 10/1992 | Corey et al. | 424/443 |
| 5,156,843 | 10/1992 | Leong et al. | 424/411 |
| 5,173,535 | 12/1992 | Abrutyn | 525/54.3 |
| 5,180,061 | 1/1993 | Khan et al. | 206/570 |
| 5,441,742 | 8/1995 | Autant et al. | 424/405 |
| 5,541,233 | 7/1996 | Roenigk | 521/54 |
| 5,639,452 * | 6/1997 | Messier | 424/78.1 |

FOREIGN PATENT DOCUMENTS

| | | | |
|---|---|---|---|
| A-40969/89 | 3/1990 | (AU) | A61L/2/18 |
| 0 084 708 A1 | 8/1983 | (EP) | A61L/9/04 |
| 0 358 572 A1 | 3/1990 | (EP) | A47L/13/17 |
| 0 473 026 A1 | 3/1992 | (EP) | A01N/25/16 |
| 0 617 074 A1 | 9/1994 | (EP) | C08J/9/00 |
| 0 641 539 A1 | 3/1995 | (EP) | A47L/13/17 |
| 1 424 692 | 2/1976 | (GB) | D21H/5/22 |
| 2 122 900 | 1/1984 | (GB) | A01N/31/02 |
| 2 299 939 | 10/1996 | (GB) | A01N/25/34 |
| 89/10691 | 11/1989 | (WO) | A01N/25/10 |
| 92/21239 | 12/1992 | (WO) | A01N/37/10 |
| 95/04459 | 2/1995 | (WO) | A01N/37/02 |

OTHER PUBLICATIONS

WPI Abstract Acc. No. 97–077938 and JP 070002615 A.
Copy of GB Patent Office Search Report for GB Application No. 9706713.6 dated Jun. 2, 1997.

* cited by examiner

*Primary Examiner*—Shelley A. Dodson
(74) *Attorney, Agent, or Firm*—Fish & Richardson P.C.

(57) ABSTRACT

Flexible articles especially hydrophilic sponges featuring long-lasting residual antimicrobial benefits, contain a carrier mass having dispersed within an effective amount of an biocidal composition such as a preservative. Process for the production of such flexible hydrophilic articles are also disclosed.

8 Claims, No Drawings

FLEXIBLE HYDROPHILIC ARTICLES ESPECIALLY SPONGES, HAVING A RESIDUAL ANTIMICROBIAL EFFECT

The present invention relates to flexible wiping articles in particular sponges, as well as woven or non-woven wipes, and the like. More specifically, the present invention relates to wiping articles having a residual long-term antimicrobial effect.

Wiping articles are commonly used in the cleaning of hard surfaces including but not limited to, glass, dishes, porcelain, lavatory fixtures, kitchen fixtures and appliances, sinks, and the like are well known. These take a variety of forms, including woven and non-woven wipes formed of fibrous (natural or synthetic) materials and in particular hydrophilic sponges. These sponges may be formed from any a variety of materials including foamed polymers as well as from cellulose. These are per se well known to the art and are very commonly encountered in food service, medical, and other environments.

A consequence of the use of such materials, particularly when used in any type of a cleaning operation is that after the sponge or wiping article has been used, it is frequently set aside in a moist state. In its moist state, it provides a place for the breeding of various bacteria, viruses, fungi, etc. Thus, these sponges and wiping articles are not sanitary.

Accordingly, there is a real and continuing need in the art for sponges and other wiping articles which have a useful antimicrobial benefit subsequent to a period of normal use in cleaning, wiping, and other operations. These objects are provided by the articles, processes, and methods of the present invention.

According to the present invention, there is provided a flexible article, desirably one which is hydrophilic, and very especially a sponge, which contain therein a carrier mass having associated therewith, desirably dispersed therein, an effective amount of an biocidal agent such as a preservative composition.

According to a further aspect of the invention there is provided a process for providing long-lasting residual anti-microbial benefit to a flexible hydrophilic article, especially a sponge which comprises the process steps of:

providing a dispersion of a biocidal composition in carrier mass having low aqueous solubility;

impregnating the said flexible hydrophilic article with the carrier mass containing the biocidal composition to provide an effective dosage of the biocidal composition to the said article.

These and other aspects of the invention will be more clearly described below.

The flexible hydrophilic articles useful in the present invention include those such as are commonly encountered and these specifically include sponges, preferably hydrophilic sponges. Useful sponges may be any variety which are presently known and many which are widely commercially available including those produced from foamed polymers such as polyurethane, polypropylene, polyethylene, polyester, polyethers, and of regenerated cellulose. Sponges which are particularly useful in the compositions of the present invention are those which are formed from cellulose and are also interchangeably referred as viscose sponges. These two are known to the art and are produced from comminuted and ground wood pulp which are then regenerated to form a porous hydrophilic article.

With regard to such sponges, it is to be understood that these may be a single material and of a single layer, or they may be produced as a composite material. What is to be understood as composite material is that two or more differing materials may be combined to form a sponge where at least one layer is hydrophilic, especially a first layer of a hydrophilic material which is glued, sewn, or otherwise connected to a second layer of a differing material. Such differing materials include those which are commonly known, including those formed of woven and/or non-woven fabric materials which are often intended to provide an abrasive surface which are not particularly deleterious to soft surfaces (Teflon®, Corian®, fiberglass, etc.). Also, such composite sponges also include those which include one or two differing hydrophilic sponge materials which may be sewn together. In this sponge construction, sponges of two different materials are sewn together at peripheral edges, and further optionally on at least one face of the sponge is further included a woven textile material. Such an exemplary sponge is available as Chore Boy® Long-Last sponges (Reckitt & Colman Inc.).

The low-aqueous soluble carrier mass is an organic material which desirably exhibits a relatively low rate of dissolution in water, generally such that when formed into a cube, exhibits less than about 5% wt. dissolution into 100 g of water (approx 20° C.) per 24 hours, and is compatible with the biocidal composition.

Exemplary organic materials which exhibit low rates of aqueous dissolution include natural waxes including vegetable waxes such as carnauba wax, cauassu wax, candelilla wax, ouricuri wax, raffia wax, palm wax, esparto wax, sugar cane wax, and cotton wax; animal waxes such as beeswax, ghedda wax, chinese insect wax, shellac wax, lanolin and walrat (spermaceti); mineral waxes such as paraffin wax, microcrystalline waxes, ozokerite-ceresin, petroleum waxes, montan wax.

Examples of synthetic waxes are fatty alcohols such as lanette wax; fatty acid esters of polyhydric alcohols and especially stearates including but not limited to glyceryl distearate, glyceryl monostearate, ethylene glycol monostearate, diethylene glycol monostearate; chlorinated products such as chlorinated naphthalane waxes, chlorinated paraffin waxes; synthetic waxes containing nitrogen such as Acrawaxes (Glycol Products Co.), Armowax (Armour Co.); pseudoester waxes such as alkylamide waxes, ester-pseudoester waxes, arylamide waxes; silicone waxes; and polyethylene waxes of both and low molecular weights, polypropylene glycol waxes and polyethylene glycol waxes such as Carbowaxes.

Mixtures of two or more waxes may also be used.

Further exemplary organic materials which exhibit which exhibit low rates of aqueous dissolution include materials which are presently commercially available in the form of surfactant compositions which include block copolymers of ethylene oxide and propylene oxide, ethoxylated alcohols, as well as alkanolamides. Mixtures of two or more of such surfactant compositions may also be used. Also, mixtures of one or more waxes may be used to form mixtures with one or more surfactant compositions described here to form the low-aqueous soluble carrier mass according to the invention. Especially preferred for use as the carrier materials having low rate of aqueous dissolution include surfactants those sold in the Plurafac® series of surfactants, particularly Plurafac® A-39 (BASF Inc., Mt. Olive Township, N.J.) as well as those sold in the Pluronic® series of surfactants, especially Pluronic® F-127 (also available from BASF Inc.)

It is contemplated that one or more of the surfactant compositions may be used, and it is further contemplated that one or more waxes may be used with one or more surfactant compounds to form the carrier materials of the invention.

With regard to the biocidal composition according to the invention, these may be virtually any which provide antimicrobial efficacy against gram positive, or gram negative, but desirably both gram positive and gram negative bacteria. Many of these materials are known and include any of a number of known preservative compositions including, but not limited to: parabens, glutaraldehyde, formaldehyde, 2-bromo-2-nitropropoane-1,3-diol, 2-methyl-4-isothiazoline-3-one, and mixtures thereof. Further useful exemplary and commercially available biocidal compositions include: Suttocide® A (50% wt. actives in solution) (Sutton Laboratories, Chatam N.J.) which is described to include an active constituent based on sodium hydroxymethylglycinate; Germaben® II (Sutton Laboratories) which is described to include an active constituent based on diazolidinyl urea, methylparaben, propylparaben and propylene glycol; Biochek® 350 (35% wt. actives) (Calgon Corp., Pittsburgh, Pa.) which is described to include an active constituent based on dodecylguanidine hydrochloride; Biochek® 410 (25% wt. actives) (Calgon Corp., Pittsburgh Pa.) described to be a preservative composition of low aqueous solubility, based on 1,2-dibromo-2,4-dicyanobutante and 1,2-benzisothiazolin-3-one; Biochek®350 (Calgon Corp., Pittsburgh, Pa.); Dowicil 75 (Dow Chemical Co., Midland Mich.); Tektamer® 38 (98% wt. actives) and Tektamer® 38AD (25.5% wt. actives in an aqeuous dispersion) (Calgon Corp.) described to include dibromo dicyanobutane as an active constituent; Proxel® GXL (19.3% wt. actives in a mixture of dipropylene glycol and water) (Zeneca Biocides, Wilmington Del.) which is described to include an active constituent based on 1,2-benzisothiazolin-3-one; Nuocept® C and Nuocept® 95 (50% wt. actives) (Hüls) which is described to include an active constituent based on polymethoxy bicyclic oxazolidine; Dantogard Plus® (Lonza Inc., Fairlawn N.J.) which is described to include an active constituent based on DMDM hydantoin and iodo propynyl butyl carbamate; Busan® 1104 (93% wt. actives) (Buckman Co.) which is described to include an active constituent based on dimethylhydroxymethylpyrazone; Busan® 1500 (93% wt. actives) (Buckman Co.) which is described to include an active constituent based on methene ammonium chloride; Dowicil® 200 (67.5% wt. actives) and Dowicil® 75 (94% wt. actives) which is described to include an active constituent based on 1-(3-chloroallyl)-3,5,7-triaza-1-azoniaadamantane chloride; Oxaban® A (78% wt. actives in an aqueous dispersion) (Angus Co.) which is described to include an active constituent based on dimethyl oxazolidine; Kathon® CG (1.5% wt. actives) and Kathon® CG/ICP (1.5% wt. actives) (both available from Rohm & Haas Co., Philadelphia Pa.) which are described to include an active constituent based on chloromethyl isothiazolinone and methyl isothiazolinone; AMA-410W® (10% wt. actives) (Vinings Co.) described to include an active constituent based methylene bis (thiocyanate); Elestab® HP100 (100% wt. actives) (Laboratoires Sérobiologiques) .) described to include an active constituent based on hexamidine diisethionate; Troysan® 142 (95% wt. actives) (Troy Chemical Co.) described to include an active constituent based on 3,5-dimethyltetrahydro 1,3,5-2H-thiadiazine-2-thione; as well as a composition marketed as Bactekiller® (Kanebo Co.) which described to include an active constituent based on silver, zinc and copper metals or metal salts.

The biocial compositions may be used individually or in mixtures or two or more, and it is only required that be not undesirably degraded when they are used in these process described hereinafter. Also, it is desired that these have at least some measure of affinity although not necessarily are required to be soluble within the carrier material within which they are dispersed, mixed, or interspersed. The biocidal composition also desirably features a low toxicity profile and thus its use in the household does not expect it to be particularly deleterious to the occupants. The biocidal composition also desirably exhibits good compatibility with a broad range of surfactant compositions especially anionic and nonionic surfactants which are optionally included in the articles according to the invention.

Others, although not particularly recited here may be used, and mixtures of two or more biocidal composition may be used.

While the efficacy of the biocidal composition selected for use may vary, and that a higher or lower dosing of biocidal composition per unit mass of the wiping article may be required, generally good results have been achieved when at least about 0.005 grams of the biocidal composition based on the weight of the actives of the biocidal composition are present per gram of wiping article based on the dry weight of the wiping article, viz., in a substantially dehydrated state. Preferably from about 0.005 grams to about 0.20 grams of the biocidal composition are present per gram of wiping article, on a dry weight basis, especially where the wiping article is a cellulose sponge. More preferably the biocidal composition, based on the weight percentage of the actives in the selected biocidal composition, is present in amounts of from 0.01 grams to 0.1 grams, still more preferably from 0.02 grams to 0.1 grams per gram of the wiping article, especially sponges, based on the dry weight of the wiping article. It is to be understood that higher dosing of the biocidal composition will also be expected to impart a longer duration of the anti-microbial properties a wiping article prepared according to the present inventive teaching. Illustrative examples of biocidal composition dosings are described in the Examples.

The wiping articles according to the invention, especially sponges, may be easily produced by a process herein the carrier material is liquefied, which may require heating, adding the biocidal composition, and thereafter stirring to ensure a good dispersion of the latter in the former. Further optional constituents including one or more surfactants may also be added. Thereafter, the mixture may be cooled, optionally molded, into a solid shape or form which may be then associated with the wiping article, or in the alternative, while still in a liquid form the wiping article may be contacted with the mixture which is subsequently permitted to cool, in situ.

As opposed to many of the prior art wiping articles, and in particularly, sponges, the sponges according to the invention provide a long-lasting antimicrobial benefit. A variety of known art sponges, wiping articles, and especially woven or non-woven wiping wipes may be provided with the benefit of a long-lasting antimicrobial benefit by following the present inventive teachings taught herein. In contrast to many of the teachings of the prior art, the selection of the preservative compositions having relatively low aqueous solubility, is not believed to be taught or anticipated in the prior art. The present known art preservative compositions, including antimicrobial quaternary ammonium compounds which are commonly used as preservative agents for sponges, specially cellulose sponges, have an appreciably higher water solubility and thus cannot provide the long-term antimicrobial benefit of the inventive wiping articles.

In accordance with the process of the invention, the wiping articles are prepared by first forming a mass or article of a carrier material within which is interspersed, mixed, or dispersed an effective amount of the biocidal composition. This may be formed by heating the carrier material to sufficient material within which it is a plastic, or more desirably is rendered fluid, and thereafter adding an effective amount of the biocidal composition and forming a mixture of these two materials. Thereafter, the material may be cooled and formed into an article such as a plate, ring, pellet, or in a further alternative preferred embodiment is used to supply an injection needle which is inserted into the interior of a wiping article, after which a quantity is injected therein and permitted to cool. According to this preferred embodiment, wiping articles, particularly sponges, may be quickly and readily produced and be provided into the interior of a sponge formed of only one type of material. However, it is to be understood that the carrier material and the biocidal composition may be formed into articles such as is described above, including pellets, rings, plates and/or rods and inserted into a pouch or other cavity formed into the interior of the sponge such as by cutting or other mechanical operation. Further, an alternative preferred embodiments of the invention with the sponges made of two or more materials it may be particularly advantageous to form the carrier material containing the biocidal composition into a flat or tubular shape, placing it between two or more layers of the sponge, and thereafter bonding the sponge together, or in the alternative fastening it by any means such as by peripheral showing about the edges of the sponge. In this way, the carrier material containing the biocidal composition is contained within the interior of the sponge, and during the lifetime of the sponge it is expected that the carrier material will slowly disperse, and with it the biocidal composition will provided into the body of the sponge.

In accordance with the further preferred embodiment of the invention, a wiping article, especially when it is in the shape of a sponge made of two or more layers of a resilient material, the carrier material containing the biocidal composition is molded into the form of a flexible sheet or flexible plate which may or may not be porous. One such form is in a cross hatched lattice or web and one part of the sponge is adhered to one side of said sheet, plate or web, while the other sponges adhere to the opposite face. As the sheet web or lattice is flexible, an advantageous degree of flexibility is imparted to the overall composite sponge construction. Once again, such a construction may be formed within the interior of a sponge having two or more layers, which may be bonded together by gluing, sewing or any other fastening arrangement including those presently known to the art.

The flexible hydrophilic articles, especially sponges, according to the invention may include one or more further constituents to enhance the overall performance of properties. One class of materials are compatible surfactants which do not deleteriously effect the overall antimicrobial benefit provided by the biocidal compositions introduced into the wiping article. These may include any of the known classes including anionic, nonionic, cationic, zwitterionic, but are desirably selected from among anionic surfactants or which are known for their good foaming and detergency properties, and from the nonionic surfactants which also provide a degree of foaming and detergency to the articles according to the invention.

Exemplary anionic surface active agents include compounds known to the art as useful as anionic surfactants. These include but are not limited to: alkali metal salts, ammonium salts, amine salts, aminoalcohol salts or the magnesium salts of one or more of the following compounds: alkyl sulfates, alkyl ether sulfates, alkylamidoether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkyl sulfoacetates, alkyl phosphates, alkyl ether phosphates, acyl sarconsinates, acyl isethionates, and N-acyl taurates. Generally, the alkyl or acyl radical in these various compounds comprise a carbon chain containing 12 to 20 carbon atoms.

Further exemplary anionic surface active agents which may be used include fatty acid salts, including salts of oleic, ricinoleic, palmitic, and stearic acids; copra oils or hydrogenated copra oil acid, and acyl lactylates whose acyl radical contains 8 to 20 carbon atoms.

Other anionic surface active agents not particularly enumerated here may also find use in conjunction with the compounds of the present invention.

With regard to nonionic surfactants, these include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

To be mentioned as particularly useful nonionic surfactants are alkoxylated linear primary and secondary alcohols such as those commercially available under the tradenames PolyTergent® SL series (Olin Chemical Co., Stamford Conn.), Neodol® series (Shell Chemical Co., Houston Tex.); as alkoxylated alkyl phenols including those commercially available under the tradename Triton(® X series (Union Carbide Chem. Co., Danbury Conn.).

Where such surfactants are included in the wiping articles of the invention, they may be supplied to the wiping article by any effective means including but not limiting to spraying, dipping, soaking a quantity of one or more surfactants dispersed or dissolved in a suitable carrier liquid which my be made us of water, organic solvents or mixtures thereof or which water is most likely to be used. Where one or more surfactants are intended to be used, and the carrier liquid is water, it is desired then that the one or more surfactants be supplied to the wiping articles prior to the process for introduction of the low biocidal composition to the wiping articles as taught herein.

According to certain and preferred embodiments of the invention, a portion of the carrier material, but generally not more than 50% by weight thereof, preferably not more than about 25% by weight thereof are substituted by a hydrophilic surfactant which provides the benefit of softening the carrier material. Such a material increases the ductility of the carrier material, while due to its hydrophilic nature also tends to be slowly dissolved in water, and thus also acts in conjunction with the carrier material in controlling the release of the biocidal composition into the sponge. Useful materials include those known to the art, and in particular include nonionic surfactants of which alkoxylated alcohols (primary or secondary, linear or branched) are particularly advantageously used. Of these, particularly useful include those sole in the Neodol® series of linear alcohol alkoxylates noted above. Certain preferred embodiments of the invention, as well as a demonstration of the long-term antimicrobial benefits of sponges according to the invention described in more fully in examples below.

EXAMPLES

The residual long-term antimicrobial benefits of the wiping articles according to the invention are demonstrated in the following. Side-by-side evaluations of a first set of "control" sponges with a second and a third set of sponges prepared and treated in accordance with the present invention was performed.

The sponges in each of the sets used in the following tests were of a tri-layer structure having a base layer of cellulose, an intermediate layer of a foamed rubber, and a top layer of a woven fabric as described in U.S. Pat. No. 4,704,757; the sponges were approximately 4 9/16th of an inch by 3 1/16th of inch by 7/8th of an inch in dimension.

Example 1

The first set of control sponges were used "as is" supplied from the manufacturer and had a dry weight (substantially dehydrated weight) of 8 grams. A 2.9 gram mixture consisting of 68.5% wt. Plurafac® A39 which at room temperature (68° F., 20° C.) is a waxy composition, and 31.5% wt. Neodol® 25-3, a $C_{12}$–$C_{15}$ ethoxylated linear alcohol with an average of 3 ethoxy groups per molecule was produced by gently heating these consistuents in a laboratory beaker to form a flowable melted mixture. While the mixture was still fluid, a large bore syringe was used to inject the 2.9 grams into the center part of the sponge in three places, each injection providing an approximately equivalent amount. This mixture was then allowed to cool and harden.

Example 2

The second set of sponges according to the invention were identical with those described immediately above and was similarly prepared but into each of the sponges was provided a mixture of about 4 grams consisting of 25% wt. of Tektamer® 38 (a preservative composition containing 1,2-dibromo-2,4-dicyanobutane), 65% wt. of Plurafac® A39 and 10% Neodol® 25-3. This mixture was similarly prepared by gently heating the constituents, and while the mixture was still fluid, a large bore syringe was used to inject the 4 grams into three places in the center part of the sponge, after which the mixture within the sponge was allowed to cool and harden.

Example 3

The third set of sponges was prepared in the same manner as the second set described above, into which was similarly injected 4 grams of a mixture which consisted of 27% wt. of Busan® 1104 (a preservative composition containing dimethylhydroxylmethylpyrazole), 50% wt. of Plurafac® A39 and 23% wt. Neodol® 25-3. As before, the mixture was prepared by gently heating the constituents to form a melted mixture, which was thereafter injected into three places in the center part of the sponge, after which the mixture within the sponge was allowed to cool and harden.

The evaluation of the residual antimicrobial benefit of the sponges was performed using an inoculum which contained both *Escherichia coli* (gram negative type pathogenic bacteria) (ATCC 8739) and *Salmonella choleraesuis* (gram negative type pathogenic bacteria) (ATCC 10708). The inoculum was prepared from a lyophilized culture of each of the indicated bacteria which was rehydrated and stored on CTA medium. Each bacteria was thereafter cultured in Trypic Soy Broth for each inoculation. During the test protocol, for each inoculation as described below, a fresh preparation of the inoculum described above was used.

The test was performed over a 15 day interval, wherein on sequential days (except for intervening weekend days of Saturday, and Sunday) each sponge in each of the sets of sponges was individually contacted with 1.0 ml of the inoculum containing the *E. coli* and *S. choleraesuis* bacteria at a concentration of log $10^6$ of each bacteria, which had been provided to a sterile hard surface. The sponges absorbed the 1.0 ml of the inoculum. Thereafter, to each of the sponges were further introduced approx. 75 ml. of Trypic Soy Broth in order to facilitate the distribution of the inoculum within the sponge, and an additional approx. 50 ml. amount of sterile deionized water was also added to further moisten the sponge and aid in distributing the inoculum within. Thereafter, each sponge was then manually wrung to remove any excess liquid, and then laid on a non-porous hard surface which was opened to the ambient environment. This protocol was performed on each of the sequential days once in the "am" (between 8–11 AM) and once in the "pm" (between 1–5 PM).

On the days indicated (see Tables 1, 2 and 3), one of the sponges was removed from each of the sets of sponges, and tested in order to determine the presence of the *E. coli* and *S. choleraesuis* bacteria.

In each test, the respective sponges were cut in half, and shortly thereafter (approx. 15 minutes to 60 minutes) one half of each sponge was therafter put through a Stomacher apparatus (Model 400 commercially available from the Tekmar Co.) to which was supplied 200 ml of Letheen broth. The stomacher was operated for a period of approximately 5 minutes, after which an aliquot of the Letheen broth was removed, serially diluted according to conventional techniques, and plated with a sterile agar medium. The aliquot of the Letheen broth was presumed to contain any *E. coli* and *S. choleraesuis* bacteria which may have been present in the sponge.

The other half of the sponge was tested in a similar manner, but were first permitted to remain on a hard surface in the laboratory and was tested on the next successive day when tests were performed, and are indicated as "am" sponges on the Tables 1, 2 and 3. This permitted for the remaining half sponge to remain in the ambient and to permit any present *E. coli* and *S. choleraesuis* bacteria to grow within the sponge. Thus, it should be understood that the test results associated with a half sponge listed as an "am" half sponge is the remaining half of the half sponge tested in the "pm" of the day prior, or in the case of intervening weekend days, was from the Friday prior.

The aliquot thus removed was used, in accordance with conventional techniques, to produce dilutions at each of $1\times10^{-1}$ through $1\times10^{-6}$ which were then plated with sterile MacConkey Agar. These plates were permitted to incubate for 36–48 hours at 35° C.–37° C. so to permit the growth of colonies of any *Escherichia coli* and/or *Salmonella choleraesuis* bacteria which may have been present.

The protocol described above was repeated during the test and the results are indicated on Table 1, 2 and 3 below. It is further to be appreciated that the sponges in the latter part of the test had been contacted for each of the days indicated above, and thus these sponges had undergone repeated cycles of contact, wringing out, lay in the ambient, until their day arrived and they were tested by being cut apart and extracted in the Letheen broth from which the number of colonies of any *Escherichia coli* and/or *Salmonella choleraesuis* bacteria which may have been present were ultimately evaluated. The results of these evaluations are indicated on Table 1 illustrating a "control" set of sponges not in accordance with the invention, and the results of Tables 2 and 3 illustrative of sponges produced according to the present invention.

tively no antimicrobial benefit. Such demonstrates that the use of such commonly encountered preservative constituents, and the dosage ranges commonly encountered of the use of these materials provides a little lasting antimicrobial benefit to the sponge under conditions typically encountered.

In contrast, as a review of the results on Tables 2 and 3 demonstrate, it may be seen that the sponges treated with

TABLE 1

(Control)

| Day | $10^{-2}$ | $10^{-3}$ | $10^{-4}$ | $10^{-5}$ | $10^{-6}$ | $10^{-7}$ | Organisms/ ½ Sponge | Organisms/ Sponge |
|---|---|---|---|---|---|---|---|---|
| 1 pm | TNTC | 30 | 3 | 0 | 0 | 0 | $3.0 \times 10^4$ | $6.0 \times 10^4$ |
| 2 am | TNTC | 56 | 6 | 0 | 0 | 0 | $5.6 \times 10^4$ | $1.1 \times 10^5$ |
| 3 pm | TNTC | TNTC | TNTC | 32 | 2 | 0 | $3.2 \times 10^6$ | $6.4 \times 10^6$ |
| 4 am | TNTC | TNTC | TNTC | TNTC | TNTC | 13 | $1.3 \times 10^8$ | $2.0 \times 10^8$ |
| 5 pm | TNTC | TNTC | TNTC | TNTC | TNTC | TNTC | $>3.0 \times 10^9$ | $>6.0 \times 10^9$ |

Testing terminated due to heavy contamination of the sponges

"TNTC" = too numerous to count

TABLE 2

(Invention - containing 1,2-dibromo-2,4-dicyanobutane)

| Day | $10^{-2}$ | $10^{-3}$ | $10^{-4}$ | $10^{-5}$ | $10^{-6}$ | $10^{-7}$ | Organisms/ ½ Sponge | Organisms/ Sponge |
|---|---|---|---|---|---|---|---|---|
| 1 pm | 0 | 0 | 0 | 0 | 0 | 0 | <100 | <100 |
| 2 am | 0 | 0 | 0 | 0 | 0 | 0 | <100 | <100 |
| 3 pm | 0 | TNTC | 0 | 0 | 0 | 0 | $4.6 \times 10^4$ | $9.2 \times 10^4$ |
| 4 am | 0 | 0 | 0 | 0 | 0 | <100 | <100 | |
| 5 pm | 0 | TNTC | 30 | 1 | 0 | 0 | $3.0 \times 10^5$ | $6.0 \times 10^5$ |
| 9 am | 0 | 0 | 0 | 0 | 0 | 0 | <100 | <100 |
| 9 pm | 0 | 46 | 24 | 4 | 0 | 0 | $4.6 \times 10^4$ | $9.2 \times 10^4$ |
| 11 am | 0 | 0 | 0 | 0 | 0 | 0 | <100 | <100 |
| 12 pm | 0 | 0 | 12 | 1 | 0 | 0 | $1.2 \times 10^4$ | $2.4 \times 10^4$ |
| 15 am | 0 | 0 | 0 | 0 | 0 | 0 | <100 | <100 |

"TNTC" = too numerous to count

TABLE 3

(Invention - containing dimethylhydroxymethylpyrazole)

| Day | $10^{-2}$ | $10^{-3}$ | $10^{-4}$ | $10^{-5}$ | $10^{-6}$ | $10^{-7}$ | Organisms/ ½ Sponge | Organisms/ Sponge |
|---|---|---|---|---|---|---|---|---|
| 1 pm | 102 | 65 | 8 | 0 | 0 | 0 | $6.5 \times 10^4$ | $1.3 \times 10^5$ |
| 2 am | 0 | 0 | 0 | 0 | 0 | 0 | <100 | <100 |
| 3 pm | TNTC | TNTC | 28 | 10 | 0 | 0 | $2.8 \times 10^5$ | $5.6 \times 10^5$ |
| 4 am | 2 | 0 | 0 | 0 | 0 | 0 | $2.0 \times 10^2$ | $4.0 \times 10^2$ |
| 5 pm | TNTC | 195 | 95 | 0 | 0 | 0 | $2.0 \times 10^5$ | $4.0 \times 10^5$ |
| 9 am | 0 | 0 | 0 | 0 | 0 | 0 | <100 | <100 |
| 9 pm | TNTC | TNTC | 66 | 10 | 1 | 0 | $6.6 \times 10^5$ | $1.3 \times 10^6$ |
| 11 am | 0 | 0 | 0 | 0 | 0 | 0 | <100 | <100 |
| 12 pm | TNTC | 53 | 18 | 0 | 0 | 0 | $5.3 \times 10^4$ | $1.0 \times 10^5$ |
| 15 am | 0 | 0 | 0 | 0 | 0 | 0 | <100 | <100 |

"TNTC" = too numerous to count

As seen from the results indicated on Table 1 (control) and Tables 2 and 3 (invention) the striking differences between the long-term antimicrobial efficacy of the sponges are demonstrated. As may be denoted from the results on Table 1, while the control sponge exhibited limited antimicrobial efficacy on the first and second day of the test, thereafter, it can be seen that the antimicrobial efficacy of the sponge substantially degraded thereafter and thus provided effectively no antimicrobial benefit. Such demonstrates that the use of such commonly encountered preservative constituents, and the dosage ranges commonly encountered of the use of these materials provides a little lasting antimicrobial benefit to the sponge under conditions typically encountered.

In contrast, as a review of the results on Tables 2 and 3 demonstrate, it may be seen that the sponges treated with these different compositions, as described above provided a striking and substantial level of efficacy against the *Escherichia coli* and/or *Salmonella choleraesuis* bacteria throughout 15 days of the test, and under the test conditions as described above. Particularly important it the fact that sponges according to the invention exhibited good long term antimicrobial efficacy subsequent to repeated dosings and rinsings.

Unlike many of the test protocols which were cited in one or more of the prior art patents, it is believed that the test protocol described herein provides a very useful and realistic test which demonstrates the unexpected and superior properties of the sponges according to the present invention. It is believed by the inventors that the performance of the test upon successive days during a two-week interval and submitting for repeated dosings with the gram negative bacteria noted above, and the demonstration of the strikingly effective long-term antimicrobial characteristics of the sponges are not believed to have been known or readily producible from the prior art.

What is claimed is:

1. A flexible wiping article into which after the flexible wiping article has been made is placed an organic material which exhibits an aqueous dissolution rate of less than about 5% wt. into 100 g of water (approx 20° C.) per 24 hours as a carrier mass, said carrier mass dispersed within itself an effective amount of one or more biocides by injection, impregnation, or molded form selected from the group consisting of pellets, rings, plates, rods, flexible sheet, flexible plate, and tubes so as to provide the flexible wiping article with a residual antimicrobial benefit.

2. A flexible wiping article according to claim 1, wherein the said wiping article is a sponge.

3. A flexible wiping article according to claim 1 wherein: the carrier mass is selected from the group consisting of: one or more synthetic waxes, microcrystalline waxes, ozokerite-ceresin, petroleum waxes, montan wax, mineral waxes, animal waxes, natural waxes, vegetable waxes, surfactant compositions based on block copolymers of ethylene oxide and propylene oxide, ethoxylated alcohols, and alkanolamides.

4. A flexible wiping article according to claim 1 wherein: the biocidal composition is present in the article in an amount of from 0.005–0.10 grams per gram of the wiping article on a dry weight basis.

5. A process for providing long-lasting residual antimicrobial benefit to a flexible hydrophilic article, which comprises the steps of:

making a flexible hydrophilic article;

fludifying a carrier mass is selected from the group consisting of one or more synthetic waxes, microcrystalline waxes, ozokerite-ceresin, petroleum waxes, montan wax, mineral waxes, animal waxes, natural waxes, vegetable waxes, surfactant compositions based on block copolymers of ethylene oxide and propylene oxide, ethoxylated alcohols, and alkanolamides which exhibit an aqueous dissolution rate of less than about 5% wt. into 100 g of water (approx 20° C.) per 24 hours;

dispersing within said fluidified water soluble carrier mass at least one biocidal composition;

subsequently providing to flexible hydrophilic article the water soluble carrier mass containing the dispersed biocidal composition in a sufficient amount in order to provide an effective dosage of the biocidal composition to the article so as to provide the flexible hydrophilic article with a residual antimicrobial benefit.

6. A process for providing long-lasting residual antimicrobial benefit to a flexible hydrophilic article according to claim 5 which further comprises the process steps of:

providing the carrier mass containing the biocidal composition into the interior of the flexible hydrophilic article; and solidifying the carrier mass.

7. A process for providing a residual antimicrobial benefit to a flexible hydrophilic article which comprises the process steps of:

making a flexible hydrophilic article;

fluidifying as a carrier mass of low aqueous solubility an organic material which exhibits an aqueous dissolution rate of less than about 5% wt. into 100 g of water (approx 20° C.) per 24 hours;

dispersing within the fluidified carrier mass a biocidal composition;

forming the carrier mass and dispersion of biocidal composition into a formed article selected from the group consisting of pellets, rings, plates, rods, flexible sheet, flexible plate, and tubes by cooling; and inserting the formed article into the interior of the flexible hydrophilic article.

8. A flexible wiping article according to claim 1 wherein the flexible wiping article is a sponge having two or more layers, which contains between the layers the molded article.

* * * * *